United States Patent [19]

Gall et al.

[11] Patent Number: 4,939,761
[45] Date of Patent: Jul. 3, 1990

[54] LIGHT DISTRIBUTOR FOR AN X-RAY DIAGNOSTICS INSTALLATION

[75] Inventors: Arthur Gall, Langensendelbach; Karl Weiss, Buckenhof, both of Fed. Rep. of Germany

[73] Assignee: Siemens Aktiengesellschaft, Berlin and Munich, Fed. Rep. of Germany

[21] Appl. No.: 216,201

[22] Filed: Jul. 7, 1988

[30] Foreign Application Priority Data

Jul. 29, 1987 [DE] Fed. Rep. of Germany ....... 8710425

[51] Int. Cl.$^5$ ............................................. H05G 1/64
[52] U.S. Cl. ...................................... 378/99; 378/62; 350/623; 350/626
[58] Field of Search ........................... 378/42, 62, 99; 358/111; 350/169–174, 422, 623, 626

[56] References Cited

U.S. PATENT DOCUMENTS

| | | | |
|---|---|---|---|
| 2,285,515 | 6/1942 | Hurley | 350/171 |
| 3,622,786 | 11/1971 | Walker et al. | 378/99 |
| 3,684,354 | 8/1972 | Koch | 350/171 |
| 4,058,833 | 11/1977 | Meyer | 358/111 |
| 4,063,092 | 12/1977 | Berdahl | 378/99 |
| 4,237,492 | 12/1980 | Roth et al. | 350/172 |
| 4,354,112 | 10/1982 | Nishio | 378/99 |
| 4,383,328 | 5/1983 | Kurihara et al. | 378/42 |
| 4,413,352 | 11/1983 | Nishio | 378/42 |
| 4,472,826 | 9/1984 | van de Ven | 378/99 |
| 4,809,309 | 2/1989 | Beekmans | 378/99 |

FOREIGN PATENT DOCUMENTS 0051430 5/1982 European Pat. Off. .
0052995 6/1982 European Pat. Off. .

Primary Examiner—Craig E. Church
Assistant Examiner—John C. Freeman
Attorney, Agent, or Firm—Hill, Van Santen, Steadman & Simpson

[57] ABSTRACT

A light distributor for directing the light of the output image of an x-ray image intensifier to a number of different types of cameras in an x-ray diagnostics installation has a housing to which the cameras are attached with their respective beam path axes disposed perpendicularly relative to each other and perpendicularly relative to the axis of the beam path from the x-ray image intensifier. A first mirror deflects the beam from the x-ray image intensifier to one of the cameras, and a second moveable mirror is introducible into the beam path between the first mirror and the first camera to deflect the beam from the x-ray image intensifier onto a second camera.

7 Claims, 2 Drawing Sheets

LIGHT DISTRIBUTOR FOR AN X-RAY DIAGNOSTICS INSTALLATION

BACKGROUND OF THE INVENTION

1. Field of the Invention

The present invention is directed to a light distributor for an x-ray diagnostics installation for directing light from the output screen of an x-ray image intensifier onto a plurality of pick-up components, such as cameras attached to the housing of the light distributor.

2. Description of the Prior Art

For displaying and/or permanently recording x-ray images in an x-ray diagnostics installation, various different types of pick-up components, such as cameras, are arranged to receive the light from the output screen of the x-ray image intensifier. Frequently more than one type of display and/or recording is desired such as, for example, a video display, a moving picture (strip film) or a photographic picture (sheet film). Thus as many as three cameras, namely a video camera, a motion picture camera and a photographic camera, may be necessary to couple to the x-ray image intensifier to obtain all of the desired formats. This requires that the light from the output screen of the x-ray image intensifier be divided or distributed so as to reach each of those cameras.

A light distributor is disclosed in U.S. Pat. No. 4,383,328 which distributes the light from the output image of the x-ray image intensifier onto two motion picture cameras and onto one video camera. A hinged, semi-reflective mirror splits the light from the output screen of the image intensifier onto the two motion picture cameras. The hinged mirror, however, remains within the beam path of one of the motion picture cameras in its standby position. A 100% reflecting mirror can be disposed in front of the hinged mirror in its standby position, the reflecting mirror being disposed perpendicularly relative to the beam path of the x-ray image intensifier. A mirror arrangement having a rotatable mirror tilted at an angle of 45° and having a reflection of 90% can be introduced into the beam path in front of the 100% reflecting mirror, the rotatable mirror permitting selecting deflection of the beam path onto one of the motion picture cameras, or onto the video camera. Although in comparison to certain other known structures, the light distributor of U.S. Pat. No. 4,383,328 exhibits a more compact structure, in fact the structural length of the unit consisting of the x-ray image intensifier and one of the motion picture cameras is enlarged in the direction of the direct beam path of the x-ray image intensifier. This makes the unit unsuitable for use in many installations, particularly those installations wherein the unit is suspended by a ceiling support and wherein the height of the installation room does not accommodate the combined length of the ceiling support and the unit.

SUMMARY OF THE INVENTION

It is an object of the present invention to provide a light distributor for directing light to a plurality of pick-up devices in an x-ray diagnostics installation which permits the pick-up devices to be arranged so that they do not contribute to the structural height of the unit in the direction of the beam path of the x-ray image intensifier.

The above object is achieved in accordance with the principles of the present invention in a light distributor which permits the pick-up components, such as cameras, to be attached thereto so that the axes of the respective beam paths of the cameras are disposed perpendicularly relative to each other and perpendicularly relative to the axis of the beam path of the x-ray image intensifier. To this end, a first mirror deflects the beam from the x-ray image intensifier onto a first camera, and a second, moveable mirror is introducible into the beam path between the first mirror and the first camera, the moveable mirror deflecting the beam from the x-ray image intensifier onto a second camera. All of the pick-up components can be laterally attached to the light distributor housing, so that they do not contribute to the structural height of the unit in the direction of the beam axis of the x-ray image intensifier.

The moveable mirror may be a semi-reflecting mirror, so that a video camera may be used as the first camera to simultaneously provide a visual display during recording of the image by the second camera. A stable and easily adjustable mounting for the moveable mirror includes two guide rods disposed obliquely relative to the x-ray image intensifier beam path between the first mirror and the first camera, the rods being disposed on opposite sides of the beam path. A carriage is provide, to which the moveable mirror is attached, which has spherical liners surrounding one of the guide rods, and engaging the other guide rod via roller bearings. A simple drive for the carriage for the moveable mirror is provided by a crank mechanism attached to the light distributor housing at one side thereof, and provided with a rotary drive.

DESCRIPTION OF THE PREFERRED EMBODIMENTS

Figure 1:
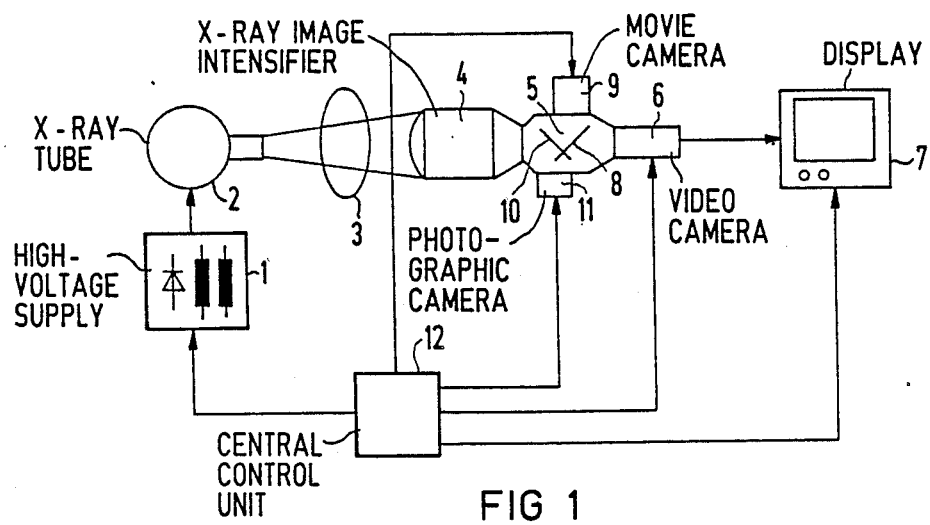
FIG. 1 is a schematic block diagram of an x-ray diagnostics installation, including a light distributor, in accordance with the teachings of the prior art.

An x-ray diagnostics installation of the type known in the prior art is schematically shown in FIG. 1. This installation includes a high voltage supply 1 for an x-ray tube 2. The x-ray tube 2 emits an x-ray beam which is attenuated by a patient 3, and the attenuated radiation is incident on the input luminescent screen of an x-ray image intensifier 4. A light distributor 5 is coupled to the output screen of the x-ray image intensifier 4. A video camera 6 is attached to the light distributor 5 as a first pick-up component, which generates video signals for displaying the output image of the x-ray image intensifier on a monitor 7.

The light comprising the output image of the x-ray image intensifier 4 is deflected to a second pick-up component, such as a motion picture camera 9, by a first moveable mirror introducible into the light beam path from the x-ray image intensifier 4. A second moveable mirror 10, also introducible into the x-ray image intensifier beam path, deflects the light in a different direction, toward a third pick-up component such as a photographic camera 11. A central control unit 12 controls and synchronizes the operation of the high-voltage generator 1, the video chain consisting of the video camera 6 and the monitor 7, movement of the mirrors 8 and 10, and the operation of the cameras 9 and 11.

When such a conventional x-ray diagnostics installation is used in a type of arrangement wherein the x-ray tube 2 is disposed beneath a patient support table, and the x-ray image intensifier and associated pick-up units are disposed above the patient support table, the room in which the installation is disposed must be able to accommodate the height of the unit formed by the x-ray image intensifier and the various pick-up components in its completely elevated position. Because the video camera 6 is disposed along the axis of the beam path from the x-ray image intensifier 4, the maximum height requirement is increased in this conventional installation to an extent that the installation may not be able to be used in certain rooms or structures.

Figure 2:
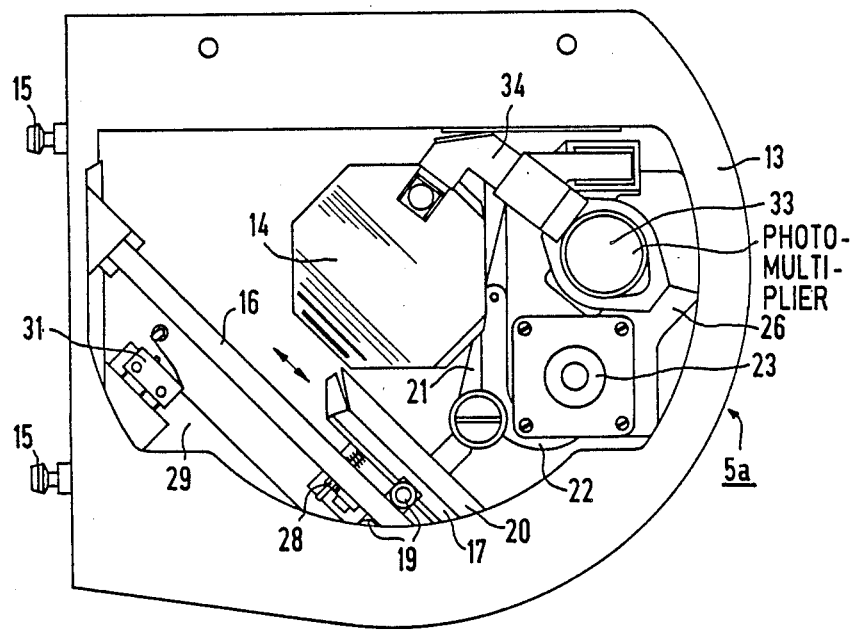
FIG. 2 is a view of a light distributor constructed in accordance with the principles of the present invention as seen from below from the perspective of the x-ray image intensifier.
Figure 3:
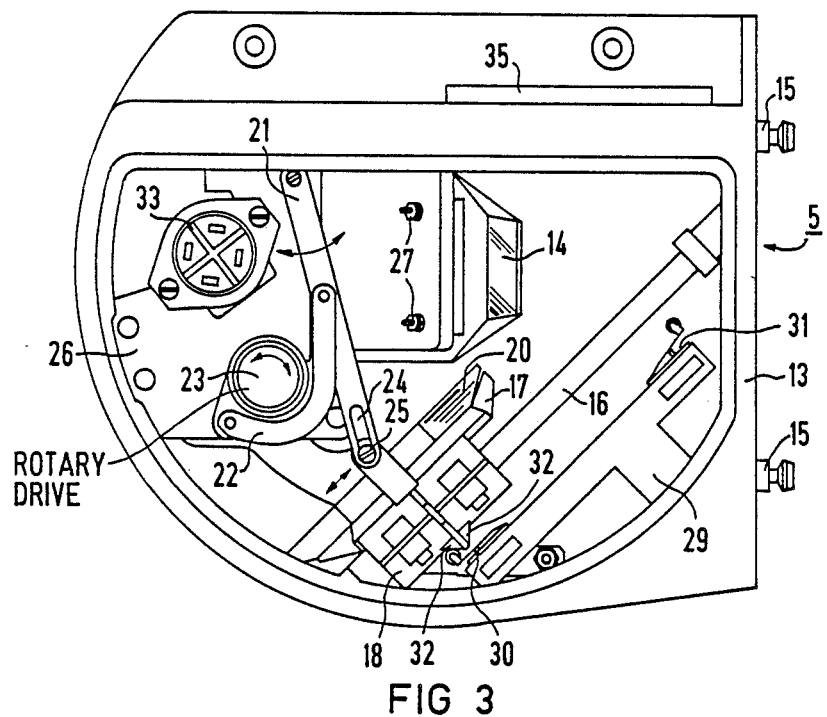
FIG. 3 is a plane view of a light distributor constructed in accordance with the principles of the present invention shown in FIG. 2.

A light distributor 5a constructed in accordance with the principles of the present invention is shown in FIG. 2 as seen from below, from the perspective of the x-ray image intensifier to which it is attached, such as the x-ray image intensifier 4 in the system shown in FIG. 1. The light distributor 5a has a housing 13 in which a first mirror 14 is disposed in the light beam path from the x-ray image intensifier. The first mirror 14 deflects the light in this beam path at substantially a right angle onto a first pick-up component, such as the video camera 6 shown in the installation of FIG. 1. The first pick-up component can be coupled to the housing 13 with fasteners 15. The first mirror 14 can be rigidly mounted in the housing 13. Two guide rods 16 are disposed in the housing 13 on opposite sides of the beam path between the first mirror 14 and the first pick-up component coupled to the housing 13. A carriage 17 is displaceable along the guide rods 16. As can be seen in FIG. 3, which shows a plan view of the light distributor 5a, the carriage 17 has spherical liners 18 embracing one of the guide rods 16, with the other side of the carriage 17 being provided with rollers 19, functioning as rolling bearings, so that the carriage 17 is moveable along the guide rods 16.

A second mirror 20 is attached to the carriage 17, functioning as a moveable mirror. The second moveable mirror 20 can be introduced with a crank mechanism (described below) into the beam path between the first mirror 14 and the first pick-up component, so that the mirror 20 deflects the light in the beam path onto a second pick-up component, such as a photographic camera or a movie camera, which can be coupled to the housing 13 at a mount 35.

The aforementioned crank mechanism includes a lever 21, a curved arm 22, and a rotary drive 23, for example, a motor. The lever 21 is pivotally mounted to the housing 13 at one end. At its opposite end, the lever 21 has an oblong opening 24, which receives a pin 25 attached to the carriage 17. The rotary drive 23 is mounted in the housing 13 on a first carrier 26. The respective positions of the mirrors 14 and 20 can be finely adjusted with adjustment screws 27 and 28.

A second carrier 29 is attached to the housing 13 beneath the carriage 17, the second carrier 29 having two microswitches 30 and 31 mounted thereon, which serve as limit switches for the moveable mirror 20. The carriage 17 is provided with noses 32 which actuate the microswitches 30 and 31 in the opposite extreme, final positions of the carriage 17.

A photomultiplier 33 is also attached to the first carrier 26, a small portion of the light of the beam path from the x-ray image intensifier being laterally coupled, in front of the first mirror 14, to the input of the photomultiplier 33 via a light guide 34. This permits the brightness of the output image of the x-ray image intensifier 4, and thus the x-ray tube radiation, to be controlled in a known manner.

Instead of the first mirror 14 being fixed, it is also possible to mount the mirror 14 so that it is either pivotable or rotatable relative to the housing 13, so that a further pick-up component can be laterally attached to the housing 13.

It is also possible to make at least the mirror 20 semi-reflective.

The light distributor 5a thus can deflect the light in the beam path from the x-ray image intensifier onto a plurality of laterally attached pick-up components, so that a low height of the light distributor 5a in the direction of the beam path from the x-ray image intensifier is achieved. At the same time, a stable mirror arrangement is provided. The unit contains only a few simple control elements, so that the light distributor 5a has a low weight, and is not particularly susceptible to mechanical disruption.

Although modifications and changes may be suggested by those skilled in the art it is the intention of the inventors to embody within the patent warranted hereon all changes and modifications as reasonably and properly come within the scope of their contribution to the art.

We claim as our invention:

1. In an x-ray diagnostics installation having an x-ray image intensifier with a beam path for light forming an output image of said x-ray image intensifier, and a plurality of pick-up components for said light, the improvement of a light distributor comprising:

a housing into which light comprises said output image of said x-ray image intensifier on said x-ray image intensifier beam path is admitted in an incoming direction;

a first mirror disposed in said housing in said x-ray image intensifier beam path which deflects said light in a direction substantially perpendicular to said incoming direction onto a first of said plurality of pick-up components;

a second mirror in said housing moveable to a position to deflect light from said beam path of said x-ray image intensifier, after deflection by said first mirror, substantially perpendicularly to said incoming direction and substantially perpendicularly to the deflection of said light by said first mirror onto a second of said plurality of said image pick-up components; and means for laterally moving said second mirror into a beam path between said first mirror and said first of said plurality of said pick-up components.

2. A light distributor as claimed in claim 1, wherein said second mirror is a semi-reflecting mirror.

3. A light distributor as claimed in claim 1, wherein said means for laterally moving said second mirror comprising:

two guide rods in said housing disposed on opposite sides of said beam path between said first mirror and said first of said plurality of said pick-up components;

a carriage to which said second mirror is attached, said carriage having means engaging each of said first and second guide rods for permitting sliding movement of said carriage along said guide rods.

4. A light distributor as claimed in claim 3, wherein said means for permitting sliding movement includes at least one spherical liner embracing one of said guide rods.

5. A light distributor as claimed in claim 3, wherein said means for permitting sliding movement includes at least one roller engaging one of said guide rods.

6. A light distributor as claimed in claim 3, wherein said means for laterally moving said second mirror further comprises a crank mechanism in said housing including a rotary drive, and means for coupling said crank mechanism to said carriage.

7. A light distributor as claimed in claim 6, wherein said crank mechanism includes a curved arm attached to said rotary drive, and wherein said means for coupling comprises:
a lever having a first end pivotally mounted in said housing and having a second end with an oblong opening therein, a pin attached to said carriage and received in said oblong opening, and means for pivotably connecting said lever to said curved arm between said first end and said opposite end.

* * * * *